United States Patent
Lai

(10) Patent No.: US 9,526,411 B2
(45) Date of Patent: *Dec. 27, 2016

(54) SYSTEM FOR MEASURING AND ANALYZING OCULAR TEMPERATURE, RECEIVING ANALYZER AND METHODS FOR USING THE SAME

(71) Applicant: Horng Ji Lai, Taipei (TW)

(72) Inventor: Horng Ji Lai, Taipei (TW)

( * ) Notice: Subject to any disclaimer, the term of this patent is extended or adjusted under 35 U.S.C. 154(b) by 26 days.

This patent is subject to a terminal disclaimer.

(21) Appl. No.: 14/517,651

(22) Filed: Oct. 17, 2014

(65) Prior Publication Data

US 2015/0119750 A1    Apr. 30, 2015

Related U.S. Application Data

(63) Continuation-in-part of application No. 14/192,504, filed on Feb. 27, 2014.

(30) Foreign Application Priority Data

Oct. 31, 2013 (TW) .............................. 102139460 A
Sep. 11, 2014 (TW) .............................. 103131266 A

(51) Int. Cl.
*A61B 3/00* (2006.01)
*A61B 5/01* (2006.01)
(Continued)

(52) U.S. Cl.
CPC .............. *A61B 3/0025* (2013.01); *A61B 3/10* (2013.01); *A61B 5/0008* (2013.01); *A61B 5/01* (2013.01); *A61B 5/6821* (2013.01)

(58) Field of Classification Search
CPC ....................................................... A61B 3/10
(Continued)

(56) References Cited

U.S. PATENT DOCUMENTS 5,297,554 A    3/1994  Glynn et al.
7,665,848 B2   2/2010  Kurtzberg et al.
(Continued)

FOREIGN PATENT DOCUMENTS

| CN | 1492735 A | 4/2004 |
| JP | 3806908 B2 | 8/2006 |
| WO | 03001991 A1 | 1/2003 |

OTHER PUBLICATIONS

Office Action dated Nov. 3, 2015 from related China Application No. 201310571720.9, 10 pages.
(Continued)

*Primary Examiner* — Michael C Stout
(74) *Attorney, Agent, or Firm* — Innovation Capital Law Group, LLP; Vic Lin

(57) ABSTRACT

A system is used to measure, record and analyze ocular surface temperature. The system comprises an ocular temperature measurement apparatus and a receiving analyzer. The ocular temperature measurement apparatus includes a temperature sensing device and a signal transmitting device. The temperature sensing device obtains data by measuring ocular surface temperature, and the signal transmitting device transmits the data through wireless signals. The receiving analyzer includes a signal receiving unit and an analyzing unit. The signal receiving unit receives the wireless signals, and based on the wireless signals, the analyzing unit analyzes and determines whether the ocular surface temperature is normal.

16 Claims, 6 Drawing Sheets

(51) Int. Cl.
*A61B 3/10* (2006.01)
*A61B 5/00* (2006.01)

(58) Field of Classification Search
USPC .......................................................... 600/549
See application file for complete search history.

(56) References Cited

U.S. PATENT DOCUMENTS

| | | | | |
|---|---|---|---|---|
| 2002/0049389 | A1* | 4/2002 | Abreu | A61B 3/1241 |
| | | | | 600/558 |
| 2008/0174733 | A1 | 7/2008 | Chang et al. | |
| 2010/0234717 | A1 | 9/2010 | Wismer | |
| 2012/0057126 | A1* | 3/2012 | Chang | G06T 7/604 |
| | | | | 351/206 |
| 2012/0245444 | A1 | 9/2012 | Otis et al. | |
| 2013/0041245 | A1 | 2/2013 | Cerboni | |
| 2013/0079660 | A1* | 3/2013 | Chang | A61B 3/101 |
| | | | | 600/549 |
| 2013/0225968 | A1* | 8/2013 | Auvray | A61B 3/16 |
| | | | | 600/398 |
| 2014/0085600 | A1* | 3/2014 | Pletcher | A61B 5/7203 |
| | | | | 351/159.03 |

OTHER PUBLICATIONS

Office Action dated Oct. 26, 2015 from related China Application No. 201410571510.4, 12 pages.
D.M. Maurice and A.S. Mushin, "Production of Myopia in Rabbits by Raised Body-Temperature and Increased Intraocular Pressure", The Lancet; Nov. 26, 1966, pp. 1160-1162.
Office Action dated Nov. 4, 2015 from corresponding U.S. Appl. No. 14/192,154, 19 pages.
Shyang-Rong Shih et al., "The Application of Temperature Measurement of the Eyes by Digital Infrared Thermal Imaging as a Prognostic Factor of Methylprednisolone Pulse Therapy for Graves' Ophthalmopathy", Acta Ophthalmologica; 2010M vol. 88, pp. 154-159.
Tien-Chun Chang et al., "Application of Digital Infrared Thermal Imaging in Determining Inflammatory State and Follow-up Effect of Methylprednisolone Pulse Therapy in Patients With Graves' Ophthalmopathy", Graefes Arch Clin Exp Ophthalmol; 2008, 246 vol., pp. 45-49.
International Search Report and Written Opinion from corresponding application No. PCT/CN2014/089274 dated Jan. 14, 2015, 16 pages.
Office Action dated Sep. 15, 2016 from corresponding U.S. Appl. No. 14/192,154, 16 pages.

* cited by examiner

SYSTEM FOR MEASURING AND ANALYZING OCULAR TEMPERATURE, RECEIVING ANALYZER AND METHODS FOR USING THE SAME

CROSS-REFERENCE TO RELATED APPLICATION

This is a continuation-in-part of patent application Ser. No. 14/192,504 filed on Feb. 27, 2014 which claims priority from Taiwan Patent Application No. 102139460 filed on Oct. 31, 2013, and further claims priority from Taiwan Patent Application No. 103131266 filed on Sep. 11, 2014, which are hereby incorporated herein by reference in its entirety.

BACKGROUND OF THE INVENTION

1. Field of the Invention

The invention relates to a system for measuring and analyzing ocular temperature, a receiving analyzer, and methods thereof, and particularly, to a system, an analyzer and methods for analyzing and determining ocular surface temperatures.

2. Description of Related Art

Ocular surface temperatures reflect the current statuses of various muscles and tissue layers of an eyeball, and hence, they can be deemed as an important index representing ocular health or some eye diseases. When there is ocular inflammation or ill-sustained accommodation (e.g. spasms) for eye muscles, the ocular surface temperature may rise. For example, pseudo-myopia or myopia happens when the ciliary muscles enter a state of spasm so that the ocular surface temperature gets higher. However, as to a dry-eyes patient, when his eyelids are closed and open, tears flowing into his eyeball surfaces get less so that the ocular surface temperature may fall. Therefore, the increase and decrease in the ocular surface temperature can be used to determine whether an eye is in good health, approaches to have pathological changes or has any pathological changes.

D. M. Maurice and A. S. Mushin indicated in "Production of Myopia in Rabbits by Raised Body-Temperature and Increased Intraocular Pressure" (The Lancet; Nov. 26, 1966, pp. 1160-1162) as follows: When the body temperature of a young rabbit raised to 41-43° C. for around 30 minutes, the refraction (dioptres) of rabbit's eye changed to below –0.75. Myopia is caused by eyes with high refractive ability. That is, incident light parallel to the visual axis of an eyeball are focused in front of its retina, and an image on retina is quite blurred. Furthermore, the changes in the visual axis are positively related to the temperature of the eyeball. The spasmodical ciliary muscles may bring the visual axis of the eyeball to be lengthened so as to result in incurable Myopia instead of pseudo-myopia. This paper also clearly showed the relation between the ocular temperature and myopia or other changes in an eye. When the temperature of an eye rises, the eyeball accordingly expands. The peripheral tissues of the eyeball can effectively withstand expansion force so that the expansion is directed toward to the posterior of the eyeball. Under such an inadequate deformation, the eyeball gradually gets longer on its visual axis.

Moreover, Tien-Chun Chang et al. metioned in "Application of digital infrared thermal imaging in determining inflammatory state and follow-up effect of methylprednisolone pulse therapy in patients with Graves' ophthalmopathy" (Graefes Arch Clin Exp Ophthalmol; 2008, 246 vol., pp. 45-49) in the following way: Digital infrared thermal imaging (DITI) has been used for measuring the local temperatures of a Graves' ophthalmopathy (GO) patient, and it also can effectively monitor and record the degree of inflammation. Further, as Shyang-Rong Shih et al. disclosed in "The application of temperature measurement of the eyes by digital infrared thermal imaging as a prognostic factor of methylprednisolone pulse therapy for Graves' ophthalmopathy" (Acta Ophthalmologica; 2010 vol. 88, pp. 164-159), after patients with GO receive intravenously methylprednisolone pulse threapy (MPT), the temperatures of their eyes averagely may decrase. The decrease in the temperature has a positive correlation with the temperature of the eye before MPT. These papers show that DITI can be used for measuring ocular temperatures and reflect the inflammatory state of GO and the follow-up effect of MPT.

Furthermore, because various kinds of electrical devices have increasingly miniaturized, wearable and embedded medical (corrective) apparatuses integrated with such electrical devices have broader applications in numerous fields. For example, U.S. Patent Application No. 2012/0245444 put forth wearable contact lenses with biochips used for detecting the concentration of a specified chemical substance in the tear fluid of an eye. U.S. Patent Application Nos. 2010/0234717 and 2013/0041245 and PCT International Patent No. 03/0001991 provide a contact lens with an electrical pressure sensor used for measuring intraocular pressure. However, very few patents or papers discussed a contact lens with an electrical temperature sensor used for measuring ocular surface temperatures. Further, none of the prior arts discloses that a contact lens having the function of temperature measurement is used to determine whether an eye are in good health or has any pathological change.

In view of above, eye treatment or vision correction is in very need of a system and a method capable of determining whether an eye is in good health or has any pathological change. It can be broadly applied to preventive medicine and correctional health.

SUMMARY OF THE INVENTION

The present application provides a system for measuring and analyzing ocular temperature, a receiving analyzer, and methods for using the same that can analyze and determine whether an eye is in good health, approaches to have pathological changes or has any pathological changes by recording the data of ocular surface temperatures. Therefore, they can be applied to preventive medicine and correctional health.

In view of above aspects, the present invention provides a system for measuring and analyzing ocular temperature, comprising:

an ocular temperature measurement apparatus for placement on an ocular surface, including:
   a temperature sensing device generating an electrical signal according to an ocular surface temperature; and
   a signal transmitting device converting the electrical signal into a wireless signal; and
a receiving analyzer, including:
a signal receiving unit receiving the wireless signal; and
an analyzing unit analyzing and determining whether the ocular surface temperature is normal according to the wireless signal.

The present invention further provides a receiving analyzer for measuring and analyzing ocular temperature, comprising:

a signal receiving unit receiving a wireless signal, wherein the wireless signal carries the data of ocular surface temperature; and an analyzing unit analyzing and determining whether the ocular surface temperature is normal according to the wireless signal.

The present invention further provides a method for measuring and analyzing ocular temperature, comprising the steps of:

measuring an ocular surface temperature by using an ocular temperature measurement apparatus for placement on an ocular surface;

transmitting data of the ocular surface temperature through a wireless signal;

receiving the wireless signal; and analyzing and determining whether the ocular surface temperature is normal according to the wireless signal.

BRIEF DESCRIPTION OF THE DRAWINGS

In order to sufficiently understand the essence, advantages and the preferred embodiments of the present invention, the following detailed description will be more clearly understood by referring to the accompanying drawings.

DETAILED DESCRIPTION OF THE INVENTION

Figure 1:
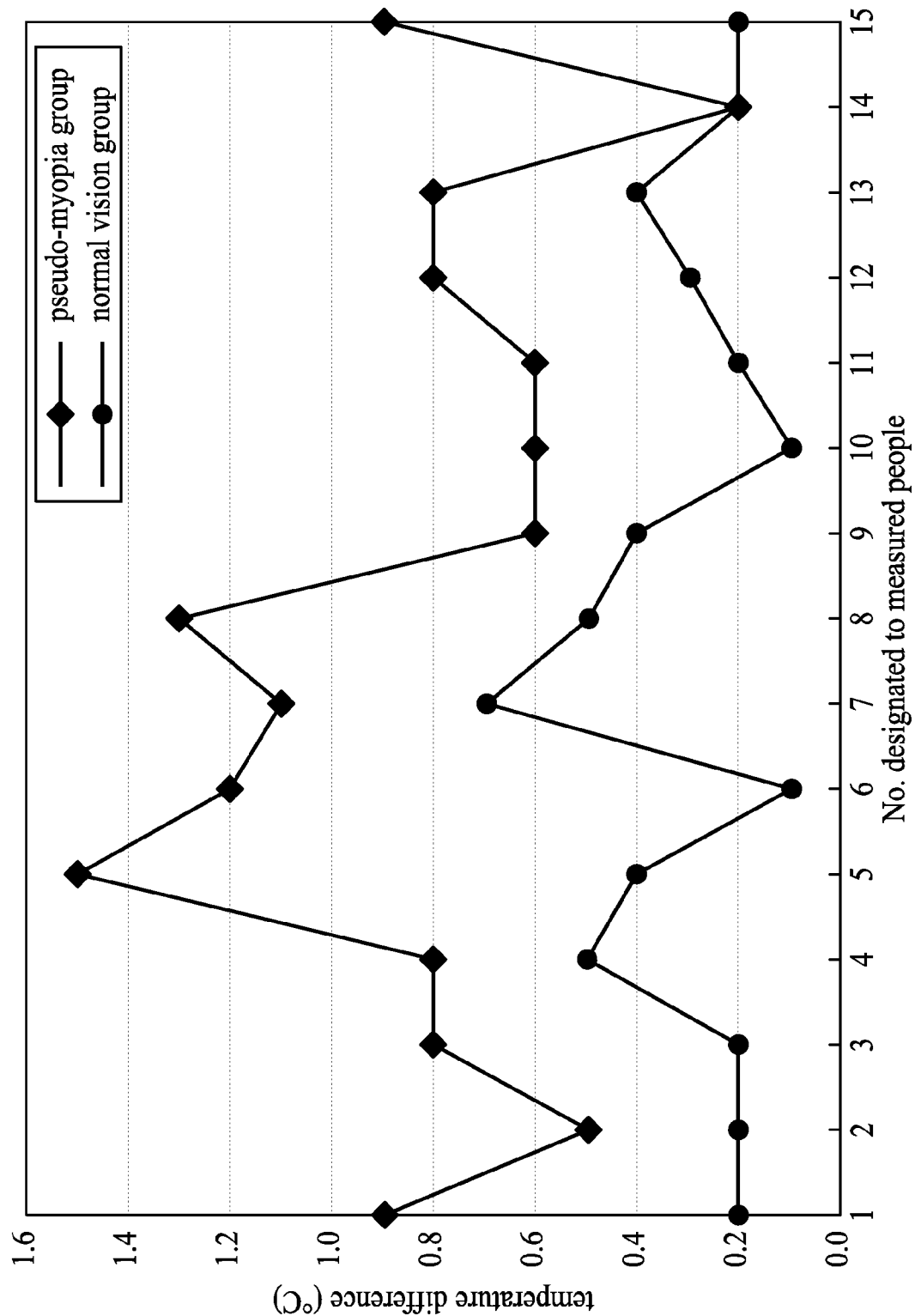
FIG. 1 is a line chart showing the differences between the daytime and nighttime ocular surface temperatures of pseudo-myopia patients and normal vision people in accordance with the present invention.

The following description shows the preferred embodiments of the present invention. The present invention is described below by referring to the embodiments and the figures. Thus, the present invention is not intended to be limited to the embodiments shown, but is to be accorded the principles disclosed herein. Furthermore, that various modifications or changes in light thereof will be suggested to persons skilled in the art and are to be included within the spirit and purview of this application and scope of the appended claims.

The drawings show a whole configuration of each embodiment in a simple and clear manner. Well known features may not have been described in detail to avoid unnecessarily obscuring the invention. Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

In the following discussion and in the claims, the terms "including", "having" or any other variation thereof, are intended to cover a non-exclusive inclusion, such that a process, method, article or apparatus that comprises a list of elements does not include only those elements but may include other elements not expressly listed or inherent to such process, method, article, or apparatus.

In view of above, the increases or decreases in an ocular surface temperature can be used for analyzing and determining whether an eye is in good health, approaches to have pathological changes or has any pathological changes. Particularly, pseudo-myopia resulted from spasmodical ciliary muscles may cause the ocular surface temperature higher. Below table 1 shows the data of ocular surface temperatures measured from the pseudo-myopia patients and normal vision people.

TABLE 1 the data of ocular surface temperatures measured from the pseudo-myopia patients and normal vision people

| | Ocular surface temperatures of pseudo-myopia patients (° C.) | | | | Ocular surface temperatures of normal vision people (° C.) | | |
|---|---|---|---|---|---|---|---|
| No. | night temp. | day temp. | temp. difference | No. | night temp. | day temp. | temp. difference |
| 1 | 34.2 | 33.3 | 0.9 | 1 | 33.8 | 33.6 | 0.2 |
| 2 | 34.0 | 33.5 | 0.5 | 2 | 32.8 | 32.6 | 0.2 |
| 3 | 35.0 | 34.2 | 0.8 | 3 | 34.2 | 34.0 | 0.2 |
| 4 | 34.8 | 34.0 | 0.8 | 4 | 34.5 | 34.0 | 0.5 |
| 5 | 34.9 | 33.4 | 1.5 | 5 | 33.1 | 32.7 | 0.4 |
| 6 | 35.1 | 33.9 | 1.2 | 6 | 33.5 | 33.4 | 0.1 |
| 7 | 35.4 | 34.3 | 1.1 | 7 | 33.9 | 33.2 | 0.7 |
| 8 | 34.7 | 33.4 | 1.3 | 8 | 33.9 | 33.4 | 0.5 |
| 9 | 33.4 | 32.8 | 0.6 | 9 | 33.1 | 32.7 | 0.4 |
| 10 | 33.5 | 32.9 | 0.6 | 10 | 34.0 | 33.9 | 0.1 |
| 11 | 33.8 | 33.2 | 0.6 | 11 | 33.4 | 33.2 | 0.2 |
| 12 | 34.0 | 33.2 | 0.8 | 12 | 33.6 | 33.3 | 0.3 |
| 13 | 34.2 | 33.4 | 0.8 | 13 | 34.3 | 33.9 | 0.4 |
| 14 | 33.8 | 33.6 | 0.2 | 14 | 33.7 | 33.5 | 0.2 |
| 15 | 34.8 | 33.9 | 0.9 | 15 | 34.0 | 33.8 | 0.2 |
| Ave. | 34.4 | 33.5 | 0.8 | Ave. | 33.7 | 33.4 | 0.3 |

Temp. is an abbreviation for temperature.
Ave. is an abbreviation for average.

Some of the prior medical papers also indicated: when the body temperature gets higher (e.g. fever) or someone stares at a near subject (e.g. book, television, computer, mobile phone and so on), in particular, with a very short distance for long time, the ciliary muscles enter a state of excessive accommodation (or in high tension) so that the ocular surface temperature accordingly rises. The temperature is gradually increased when the ciliary muscles have higher tension. Even though the ciliary muscles are overused during daytime, the tensioned ciliary muscles may get release at nighttime when the one goes to sleep. The heat is then released out from the ciliary muscles to the other parts of the eye. However, during a sleeping period, the heat dissipated from the ocular surface is blocked by the eyelid so that the ocular temperature is difficult to be lower or even cannot fall. On the other hand, eye's orientation is different when body's gesture changes (e.g. laid flat) at sleeping time, and hence, the peripheral pressures of the vitreous body may get higher. Therefore, the heat and pressures are directed to the posterior portion of an eyeball from its interior. Days after days, the vision axis is prolonged. The image is then formed in front of the retina so that the myopia is developed.

FIG. 1 is a line chart showing the differences between the daytime and nighttime ocular surface temperatures of pseudo-myopia patients and normal vision people in accordance with the present invention. As shown in the chart, the differences between the day and night ocular surface temperatures of pseudo-myopia patients are quite larger than those of the normal vision people. That is, the nighttime ocular surface temperatures are apparently higher than the daytime ocular surface temperatures for the pseudo-myopia patients. By contrast, the differences between the day and night ocular surface temperatures of the normal vision people are smaller. The nighttime ocular surface temperatures are slightly higher than the daytime ocular surface temperatures for the normal vision people. Therefore, the record of ocular surface temperatures can be used to analyze and determine whether an eye is in good health, approaches to have pathological changes or has any pathological changes. It can be applied to preventive medicine and correctional health. The present invention is not limited to the diagnosis of myopia. Dry-eye or a symptom of any eye diseases reflecting the temperature changes can also be applied to various embodiments of the present application. Furthermore, the requirements of each embodiment can be modified according to the range and tendency of temperature changes. FIG. 1 shows that the ocular surface temperatures of two groups are measured at daytime and nighttime. The present invention also can adapt the average of the differences between the daytime and nighttime ocular surface temperatures of the same one for a long term, the maximum or average of the ocular surface temperatures of the same one at the same time point each day, the ocular surface temperatures during a specified period or the differences and variation of the average temperatures during a specified period. The present invention is not limited to the foregoing embodiments. The differences and averages of the ocular surface temperatures can be applied to the present invention.

In view of above, the increases or decreases in an ocular surface temperature can be used for analyzing and determining whether an eye is in good health, approaches to have pathological changes or has any pathological changes. Particularly, dry-eye caused by either decreased tear production or increased tear film evaporation may apparently vary the ocular surface temperature. Below table 2 shows the data of ocular surface temperatures measured from two groups of dry-eye patients and normal vision people.

TABLE 2 the data of ocular surface temperatures measured from two groups of dry-eye patients and normal vision people

| Ocular surface temperatures of dry-eye patients (° C.) | | | | Ocular surface temperatures of normal vision people (° C.) | | | |
| --- | --- | --- | --- | --- | --- | --- | --- |
| No. | To | Tc | Td | No. | To | Tc | Td |
| 1 | 34.3 | 34.1 | 0.2 | 1 | 33.8 | 33.2 | 0.6 |
| 2 | 34.3 | 34.0 | 0.3 | 2 | 34.1 | 33.6 | 0.5 |
| 3 | 33.8 | 33.7 | 0.1 | 3 | 34.2 | 33.6 | 0.6 |
| 4 | 34.1 | 33.9 | 0.2 | 4 | 33.9 | 33.5 | 0.4 |
| 5 | 34.0 | 33.8 | 0.2 | 5 | 33.9 | 33.4 | 0.5 |
| 6 | 33.3 | 33.1 | 0.2 | 6 | 33.5 | 33.0 | 0.5 |

TABLE 2-continued the data of ocular surface temperatures measured from two groups of dry-eye patients and normal vision people

| Ocular surface temperatures of dry-eye patients (° C.) | | | | Ocular surface temperatures of normal vision people (° C.) | | | |
| --- | --- | --- | --- | --- | --- | --- | --- |
| No. | To | Tc | Td | No. | To | Tc | Td |
| 7 | 33.9 | 33.5 | 0.4 | 7 | 33.7 | 33.4 | 0.3 |
| Ave. | 33.96 | 33.73 | 0.23 | Ave. | 33.87 | 33.39 | 0.49 |

Temp. is an abbreviation for temperature.
Ave. is an abbreviation for average.
To: The ocular surface temperature is immediately taken when the eye is just open after blinking.
Tc: The ocular surface temperature is taken again at the 6th second (or any time point within the 6th second to the tenth second) when the eye still keeps open.
Td: The temperature difference is between To and Tc.

According to the data listed in Table 2, the differences Td of the dry-eye patients are apparently lower than the differences Td of the normal vision people. Therefore, the dry-eye syndrome can be estimated based on the foregoing fact in the following way: When the difference Td is smaller than 0.2° C., the possibility of dry-eye syndrome is high; when the difference Td is between 0.2 to 0.4° C., the possibility of dry-eye syndrome is fifty to fifty; when the difference Td is larger than 0.4° C., the possibility of dry-eye syndrome is low. The present invention is not limited to the embodiments. Either a temperature To or a temperature Tc can be adapted for another estimation rule, or the tendency variation (abrupt increase, abrupt decrease, gradual increase and gradual decrease) or slope variation of a curve plotted by some temperatures To or temperatures Tc can also be adapted for various estimation rules. The occurrences of different eye diseases can be practically estimated according to an estimation rule which is obtained by changing the content or determination way of the foregoing estimation rules.

Figure 2:
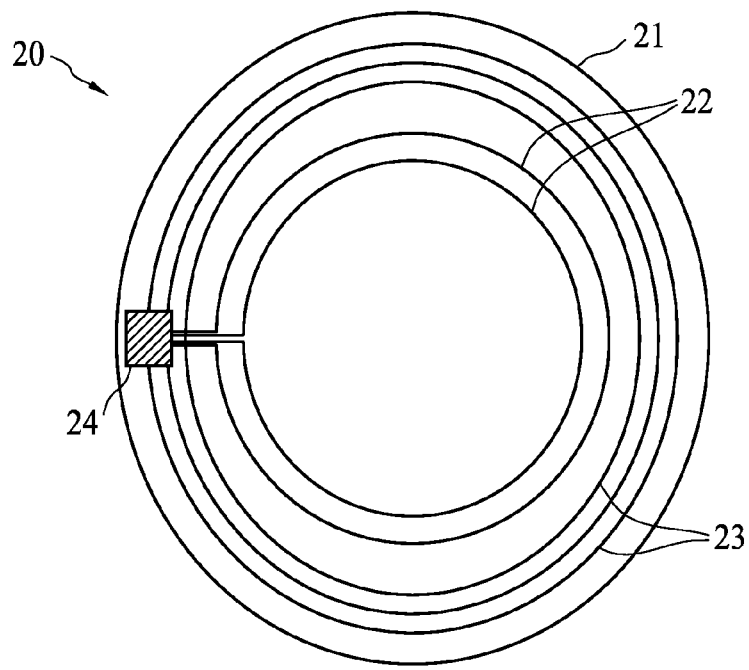
FIG. 2 is a schematic diagram of an ocular temperature measurement apparatus in accordance with the present invention.

FIG. 2 is a schematic diagram of an ocular temperature measurement apparatus in accordance with the present invention. In this embodiment, the ocular temperature measurement apparatus is, but is not limited to, a contact lens 20 with a temperature measurement function. It can be various wearable apparatuses placed on an ocular surface for measuring an ocular temperature. The contact lens 20 mainly comprises a transparent substrate 21, a temperature sensing device (temperature sensing circuit) 22, an antenna 23 and a signal transmitting device 24. The material of the transparent substrate 21 can be silicone hydrogel (e.g. Hydroxyethyl methacrylate (HEMA)) which has the advantages of high levels of oxygen permeability and hydrophily. Therefore, a user can feel more comfortable with the contact lens within a long period. The material of the transparent substrate 21 can be other transparent polymer materials, but is not limited to the example. The antenna 23 can transmit wireless signals outwards and also can receive external energy. For example, electrical power is generated through the inductive link or inductive coupling effect between radio frequency (RF) signals (or other electromagnetic waves) and the antenna 23. The electrical power can accordingly charge the temperature sensing device 22 and the signal transmitting device 24. Furthermore, a power supply apparatus capable of generating radio frequency signals or electromagnetic waves can be disposed in one's headscarf or pocket, or can be integrated into a portable apparatus (e.g. mobile phone, Bluetooth earphone, etc.), but the present invention is not limited to the examples. Also, a MEMS (Micro Electro-Mechanical Systems) battery can be disposed in the surface or internal of the transparent substrate 21.

Because the area of the contact lens 20 is limited, the number or dimension of coils of the antenna 23 is quite restricted. To compensate the possibly insufficient intensity of signals from the antenna 23, an external antenna 33 (See FIG. 3) can be attached to an area closed to the eye (e.g. orbit). Therefore, the signal can be redirected and strengthened so that a remote signal receiving apparatus can clearly receive it.

In order to monitor the variations in daytime and/or sleeping-time ocular temperature within a long period, several ring-like wirings (i.e. temperature sensing device 22) capable of sensing temperatures are printed on the surface of the transparent substrate 21, and are concentric to the contact lens 20. The ring-like wirings can be several circular wirings, polygonal wirings or irregular ring-like wirings. The temperature sensing device 22 can be an ASIC (Application-Specific IC), a MEMS device, or a sensing device formed by a nano or peco chemical material, metal material or bio material. They can measure temperatures or respond to the variations in temperatures. Furthermore, the signal transmitting device 24 converts the electrical signals (e.g. voltage signals or current signals) generated from the temperature sensing device 22 into RF signals, and wireless signals are sent outwards by the antenna 23. The present invention is not limited to the embodiment. The electrical signals also can be converted into signals conforming to a protocol such as Bluetooth and WiFi. Similar to the foregoing ring-like wirings, the antenna 23 is coated on the surface of the transparent substrate 21 and disposed outside the temperature sensing device 22 as several ring-like wirings. It transmits wireless signals conforming to a communication protocol outwards.

Figure 3:
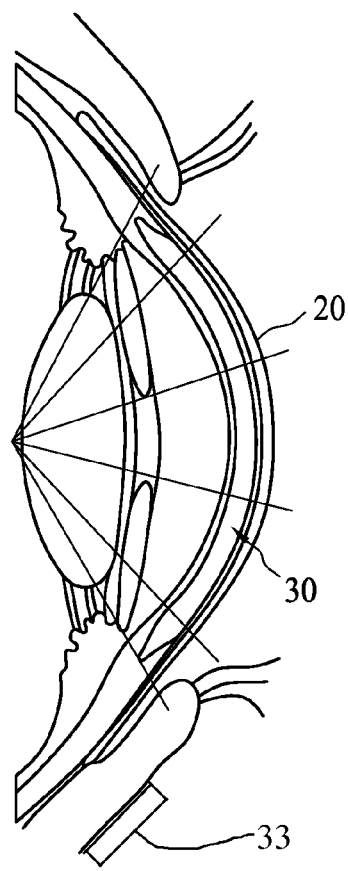
FIG. 3 is a schematic diagram showing an eye wearing the ocular temperature measurement apparatus in FIG. 2 in accordance with the present invention.

FIG. 3 is a schematic diagram showing an eye wearing the ocular temperature measurement apparatus in FIG. 2 in accordance with the present invention. As shown in this figure, when a measured one puts the contact lens 20 on the surface of an eyeball 30, he not only wears it at sleeping time but also can comfortably wear it during daytime activities for measurement because the ring-like wirings of the temperature sensing device 22 and the antenna 23 are disposed on the invisible areas (outside pupil) of the contact lens and cannot block the light incident to the pupil. The one can long-termly wear the contact lens 20 with the temperature measurement function during either life time or working time, and does not need to stay at a measurement area for just being closed to a temperature measurement tool. For example, the prior art asked the one under measurement to stand in front of an IR (infrared) measurement gauge. The present invention is suitable for measurement during an activity, sleep or long period so that the accuracy of the syndrome estimation is quite improved.

Figure 4:
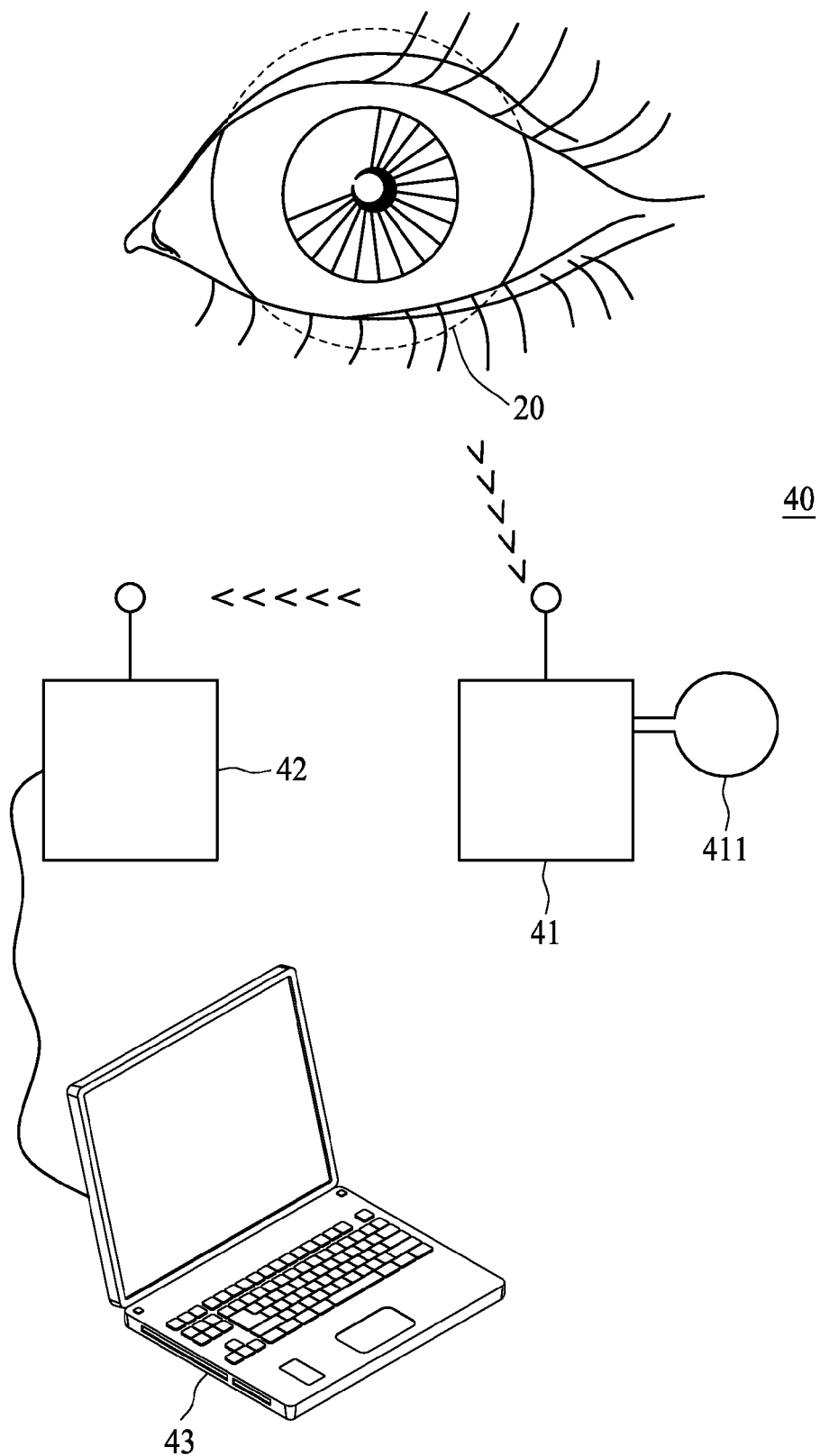
FIG. 4 is a schematic diagram showing a system for measuring and analyzing an ocular surface temperature in accordance with the present invention.

FIG. 4 is a schematic diagram showing a system for measuring and analyzing an ocular surface temperature in accordance with the present invention. The system 40 comprises a contact lens 20, a mobile interrogation unit 41, a data receiving unit 42 and a computer 43. The mobile interrogation unit 41 powers the signal transmitting device 24 and the temperature sensing device 22 through a ring-like inductive loop 411 in a wireless way, and receives wireless signals including the data of the ocular surface temperature. The wireless signals are modulated to obtain electrical signals. Then, the electrical signals are converted into digital signals or digital data related to the electrical signals through analog-to-digital conversion. The digital data are carried on carrier waves through modulating conversion to have a RF signal. The data receiving unit 42 receives the RF signal from the mobile interrogation unit 41 in a wireless manner, and modulates the RF signal to retrieve the digital data related to the electrical signals. The computer 43 stores a relation table (or a look-up table) between the digital data and ocular surface temperatures, and is electrically connected to the data receiving unit 42 to receive the digital data. According to the relation table, the computer 43 can find a corresponding ocular surface temperature and displays and stores it.

The computer 43 can analyze the stored ocular surface temperature and determine whether the ocular surface temperature is normal. For example, the myopia or pseudo-myopia syndrome can be confirmed according to the differences (See Table 1) between the daytime and nighttime ocular surface temperatures as follows: When the difference is smaller than 0.1° C., the possibility of myopia syndrome is quite low; when the difference is between 0.1 to 0.3° C., the possibility of myopia syndrome is fifty to fifty; when the difference is larger than 0.3° C., the possibility of myopia syndrome is high. The foregoing estimation result can be shown on the screen of the computer 43 or displayed by the indicator lamps of the data receiving unit 42. For example, a green lamp represents no possible for the myopia syndrome, a yellow lamp represents some possible and a red lamp represents high possible. The present invention is not limited to the estimation rules of the foregoing embodiment. The estimation rules can be determined according to practical ocular surface temperatures.

The mobile interrogation unit 41, the data receiving unit 42 and the data analyzing and determining unit (the computer 43 in the embodiment) can be integrated into a receiving and analyzing apparatus. The receiving and analyzing apparatus can be a computer installed with specified software or an application program, a panel computer, a smart phone or a smart wrist watch. The ring-like inductive loop 411 is combined with the foregoing apparatus or embedded into it.

Figure 5:
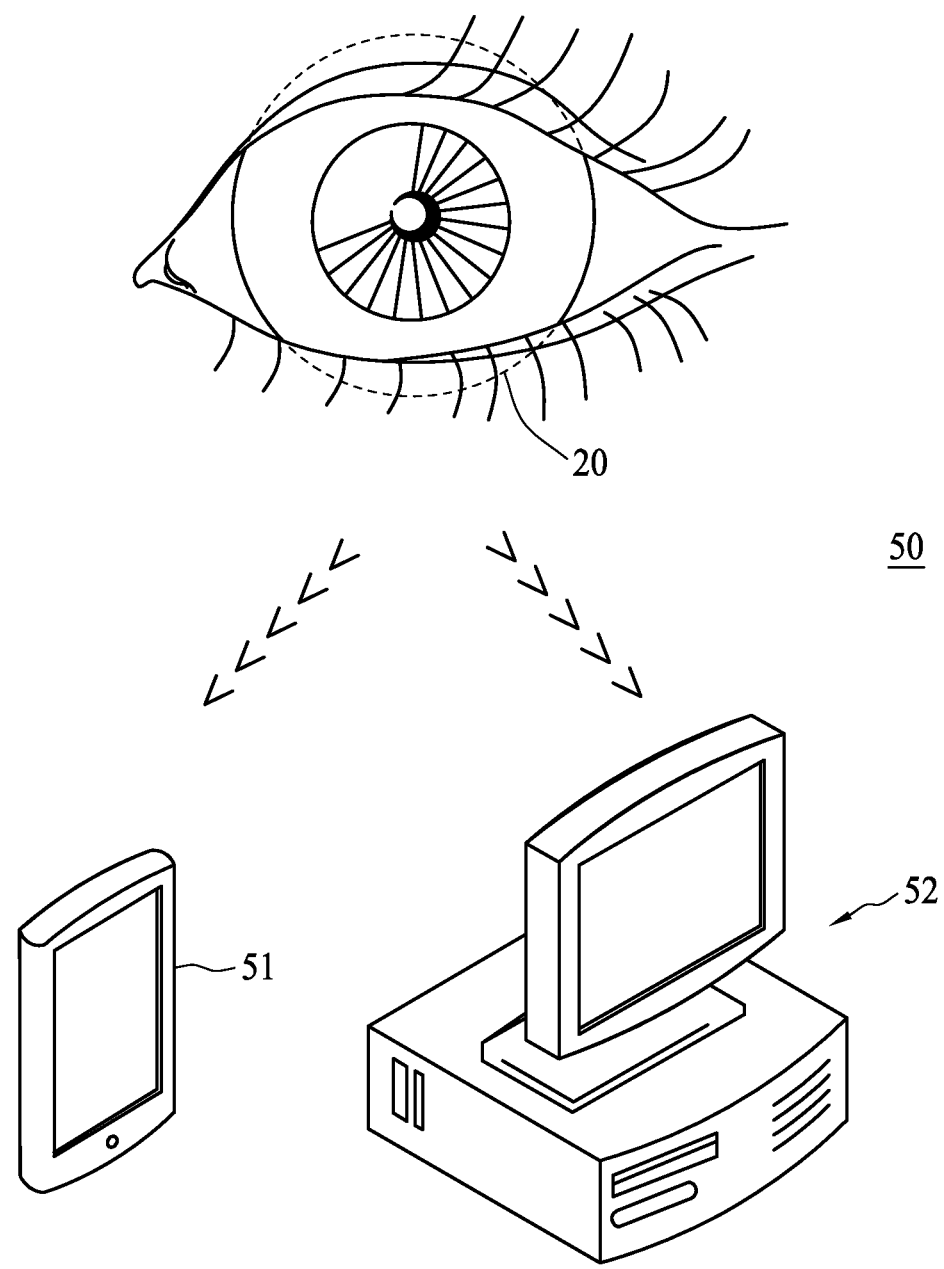
FIG. 5 is a schematic diagram showing a system for measuring and analyzing an ocular surface temperature in accordance with another embodiment of the present invention.

FIG. 5 is a schematic diagram showing a system for measuring and analyzing an ocular surface temperature in accordance with another embodiment of the present invention. A system 50 utilizes a mobile phone 51 or a desk computer 52 as a receiving and analyzing apparatus which includes a signal receiving unit and an analyzing unit. The signal receiving unit receives wireless signals generated from the contact lens 20, and the analyzing unit can analyze and determine whether the ocular surface temperature is normal according to the wireless signals.

Figure 6:
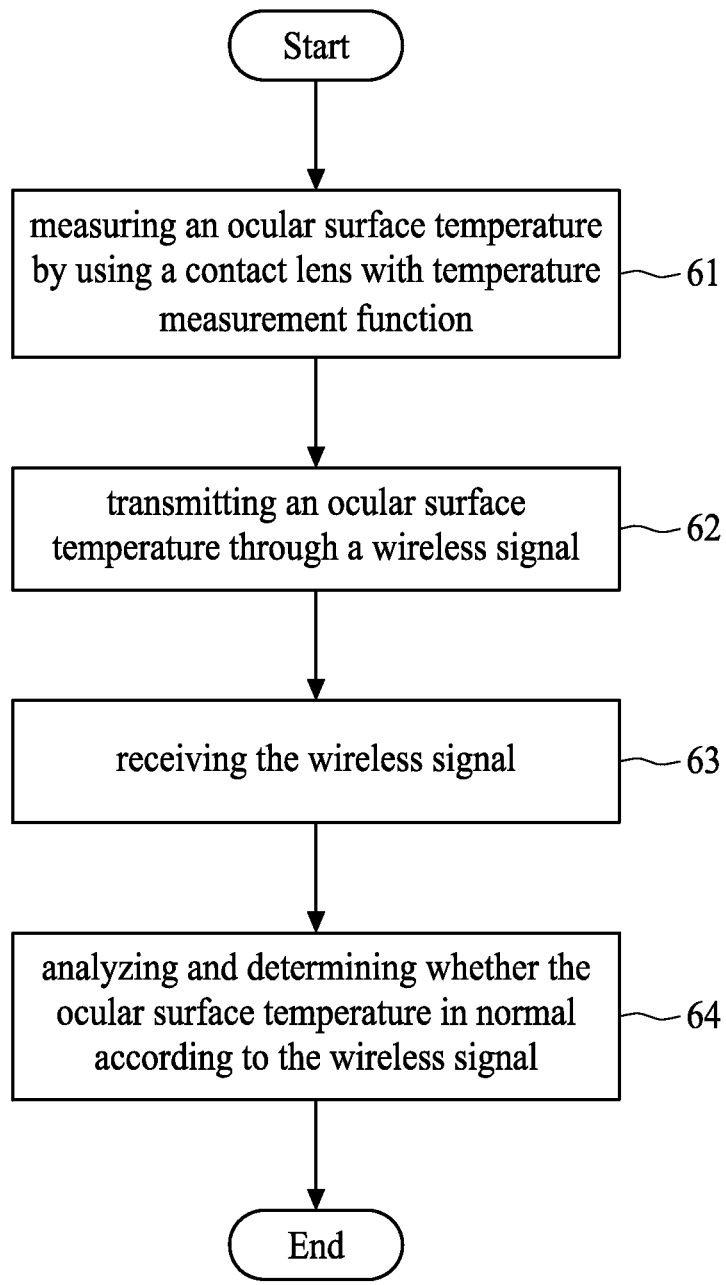
FIG. 6 is a flow chart showing a method for measuring and analyzing an ocular surface temperature in accordance with the present invention.

FIG. 6 is a flow chart showing a method for measuring and analyzing an ocular surface temperature in accordance with the present invention. The present application further provides a method for measuring and analyzing ocular temperature, comprising the steps of: as shown in Step 61, measuring an ocular surface temperature by using a contact lens with a temperature measurement function; as shown in Step 62, transmitting data of the ocular surface temperature through a wireless signal; as shown in Step 63, receiving the wireless signal; and as shown in Step 64, analyzing and determining whether the ocular surface temperature is normal according to the wireless signal.

Figure 7:
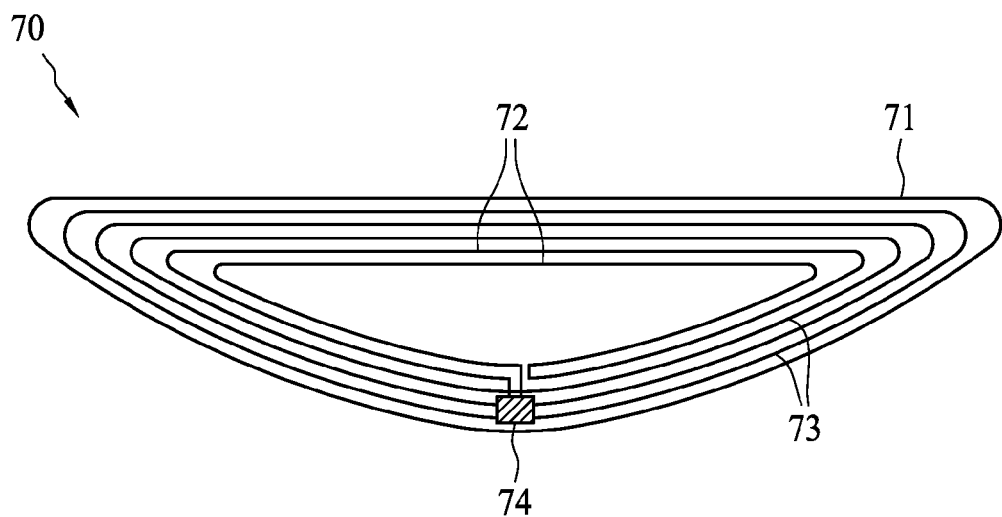
FIG. 7 is a schematic diagram of an ocular temperature measurement apparatus in accordance with another embodiment of the present invention.

Compared with the contact lens 20 in FIG. 3, FIG. 7 is a schematic diagram of an ocular temperature measurement apparatus in accordance with another embodiment of the present invention. When the ocular temperature measurement apparatus 70 in this embodiment is worn on an ocular surface, it does not cover the pupil. Furthermore, the apparatus of this embodiment is also applicable to the system for measuring and analyzing an ocular surface temperature, and is electrically powered by the mobile interrogation unit 41 and transmits wireless signals containing the data of ocular surface temperatures. The ocular temperature measurement apparatus 70 mainly comprises a substrate 71, a temperature sensing device (temperature sensing circuit) 72, an antenna 73 and a signal transmitting device 74. The material of the substrate 71 can be silicone hydrogel, polyester or Polyacrylamide (PAM), and is transparent, translucent or opaque. The substrate 71 can be made by other polymers which are hard or soft. For example, but is not limited to, silicone polymer or polymethylmethacrylate (PMMA) is formed in a shape which is suitable for an eyeball). The antenna 73 can transmit wireless signals outwards and also can receive external energy. For example, electrical power is generated through the inductive link or inductive coupling effect between radio frequency (RF) signals (or other electromagnetic waves) and the antenna 73. The electrical power can accordingly charge the temperature sensing device 72 and the signal transmitting device 74. Also, a MEMS (Micro Electro-Mechanical Systems) battery can be disposed in the surface or internal of the substrate 71 to directly power the temperature sensing device 72 and the signal transmitting device 74.

Because the ocular temperature measurement apparatus 70 is placed behind an eyelid (See FIG. 8), its area is quite limited and the number or dimension of coils of the antenna 73 is quite restricted. To compensate the possibly insufficient intensity of signals from the antenna 73, an external antenna can be attached to an area closed to the eye (e.g. orbit). Therefore, the signal can be redirected and strengthened so that a remote signal receiving apparatus can clearly receive it.

In order to monitor the variations in daytime and/or sleeping-time ocular temperature within a long period, several ring-like wirings (i.e. temperature sensing device 72) capable of sensing temperatures are printed on the surface of the substrate 71. The ring-like wirings can be several circular wirings, polygonal wirings or irregular ring-like wirings. The temperature sensing device 72 can be an ASIC (Application-Specific IC), a MEMS device, or a sensing device formed by a nano or peco chemical material, metal material or bio material. They can measure temperatures or respond to the variations in temperatures. Furthermore, the signal transmitting device 74 converts the electrical signals (e.g. voltage signals or current signals) generated from the temperature sensing device 72 into RF signals, and wireless signals are sent outwards by the antenna 73. The present invention is not limited to the embodiment. The electrical signals also can be converted into signals conforming to a protocol such as Bluetooth and WiFi. Similar to the foregoing ring-like wirings, the antenna 73 is coated on the surface of the substrate 71 and disposed outside the temperature sensing device 72 as several ring-like wirings. It transmits wireless signals conforming to a communication protocol outwards.

Figure 8:
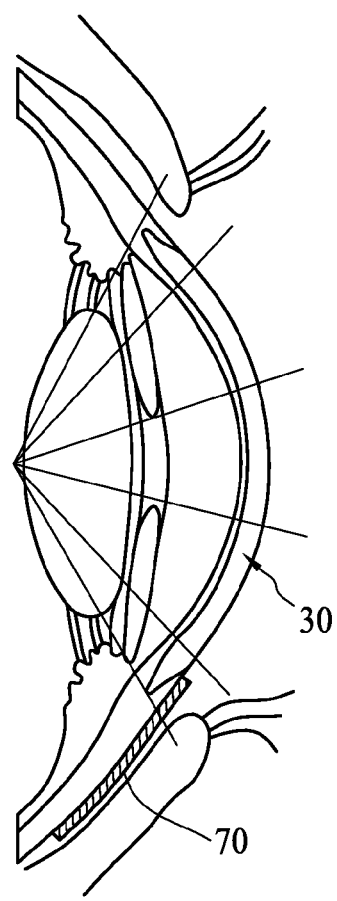
FIG. 8 is a schematic diagram showing an eye wearing the ocular temperature measurement apparatus in FIG. 7 in accordance with the present invention.

FIG. 8 is a schematic diagram showing an eye wearing the ocular temperature measurement apparatus in FIG. 7 in accordance with the present invention. As shown in this figure, when a measured one puts the ocular temperature measurement apparatus 70 on the surface of an eyeball 30 and behind an eyelid (an upper eyelid or a lower eyelid), he not only wears it at sleeping time but also can comfortably wear it during daytime activities for measurement because the whole substrate 71 is disposed on an invisible area (outside pupil). In this regard, the substrate 71 can be made by an opaque material without considering whether it blocks the light incident to a pupil. The substrate 71 can be made in a crescent (See FIG. 8), semicircle or rectangular shape so as to be easily placed behind an eyelid.

The foregoing embodiments of the invention have been presented for the purpose of illustration. Although the invention has been described by certain preceding examples, it is not to be construed as being limited by them. They are not intended to be exhaustive, or to limit the scope of the invention. Modifications, improvements and variations within the scope of the invention are possible in light of this disclosure.

What is claimed is:

1. A system for measuring and analyzing ocular temperature of an eye, comprising:
    an ocular temperature measurement apparatus for placement on an ocular surface, including:
        a temperature sensing device generating an electrical signal according to an ocular surface temperature; and
        a signal transmitting device converting the electrical signal into a wireless signal; and
    a receiving analyzer, including:
        a signal receiving unit receiving the wireless signal; and
        an analyzing unit analyzing and determining whether the ocular surface temperature is normal according to the wireless signal, wherein the analyzing unit calculates a difference between two values of the ocular surface temperature respectively at daytime and nighttime and, when the difference is below a lower threshold value, an indication is provided to a user indicating that the eye has no myopia or pseudo-myopia.

2. The system for measuring and analyzing ocular temperature according to claim 1, wherein the ocular temperature measurement apparatus further comprises an antenna transmitting wireless signals outwards, wherein the antenna generates electrical power through inductive coupling with external electromagnetic waves for powering the temperature sensing device and the signal transmitting device.

3. The system for measuring and analyzing ocular temperature according to claim 2, further comprising an external antenna directing the wireless signal.

4. The system for measuring and analyzing ocular temperature according to claim 1, wherein the analyzing unit determines that the eye may have myopia or pseudo-myopia when the difference is between the lower threshold value and a higher threshold value, or the analyzing unit determines that the eye has myopia or pseudo-myopia when the difference is above the higher threshold value.

5. The system for measuring and analyzing ocular temperature according to claim 1, wherein the analyzing unit determines that the eye has dry-eye when a difference between another two values of the ocular surface temperature respectively measured at two time points is below a lower threshold value.

6. The system for measuring and analyzing ocular temperature according to claim 5, wherein one of the another two values is immediately measured when the eye is just open after blinking and the other is measured within the sixth second to the tenth second when the eye still keeps open.

7. The system for measuring and analyzing ocular temperature according to claim 6, wherein the analyzing unit determines that the eye may have dry-eye when the difference between the another two values is between 0.2 to 0.4°

C., or the analyzing unit determines that the eye may not have dry-eye when the difference between the another two values is above 0.4° C.

8. The system for measuring and analyzing ocular temperature according to claim 1, wherein the receiving analyzer includes:
a mobile interrogation unit powering the signal transmitting device and the temperature sensing device and receiving the wireless signal for generating an RF signal; and
a data receiving unit receiving the RF signal for converting the RF signal into data including the ocular surface temperature.

9. A receiving analyzer for measuring and analyzing ocular temperature of an eye, comprising: a signal receiving unit receiving a wireless signal, wherein the wireless signal carries the data of ocular surface temperature; and an analyzing unit analyzing and determining whether the ocular surface temperature is normal according to the wireless signal; wherein the analyzing unit calculates a difference between two values of the ocular surface temperature respectively at daytime and nighttime and, when the difference is below a lower threshold value, an indication is provided to a user indicating that the eye has no myopia or pseudo-myopia.

10. The receiving analyzer for measuring and analyzing ocular temperature according to claim 9, wherein the analyzing unit determines that the eye may have myopia or pseudo-myopia when the difference is between the lower threshold value and a higher threshold value, the analyzing unit determines that the eye has myopia or pseudo-myopia when the difference is above the higher threshold value, or the analyzing unit determines that the eye has dry-eye when a difference between another two values of the ocular surface temperature respectively measured at two time points is below a lower threshold value.

11. The receiving analyzer for measuring and analyzing ocular temperature according to claim 10, wherein one of the another two values is immediately measured when the eye is just open after blinking and the other is measured within the sixth second to the tenth second when the eye still keeps open.

12. The receiving analyzer for measuring and analyzing ocular temperature according to claim 11, wherein the analyzing unit determines that the eye may have dry-eye when the difference between the another two values is between 0.2 to 0.4° C., or the analyzing unit determines that the eye may not have dry-eye when the difference between the another two values is above 0.4° C.

13. The receiving analyzer for measuring and analyzing ocular temperature according to claim 9, wherein the receiving analyzer includes:
a mobile interrogation unit powering a signal transmitting device and a temperature sensing device and receiving the wireless signal for generating an RF signal; and
a data receiving unit receiving the RF signal for converting the RF signal into data including the ocular surface temperature.

14. A method for measuring and analyzing ocular temperature of an eye, comprising the steps of: measuring an ocular surface temperature by using a contact lens with a temperature measurement function; transmitting data of the ocular surface temperature through a wireless signal; receiving the wireless signal into an analyzing unit; analyzing and determining, by the analyzing unit, whether the ocular surface temperature is normal according to the wireless signal; and calculating a difference between two values of the ocular surface temperature respectively at daytime and nighttime and, when the difference is below a lower threshold value, an indication is provided to a user indicating that the eye has no myopia or pseudo-myopia.

15. The method for measuring and analyzing ocular temperature according to claim 14, wherein the wireless signals conform to a communication protocol.

16. The method for measuring and analyzing ocular temperature according to claim 14, wherein the analyzing unit determines that the eye may have myopia or pseudo-myopia when the difference is between the lower threshold value and a higher threshold value, the analyzing unit determines that the eye has myopia or pseudo-myopia when the difference is above the higher threshold value, or the analyzing unit determines that the eye has dry-eye when a difference between another two values of the ocular surface temperature respectively measured at two time points is below a lower threshold value.

* * * * *